June 24, 1975 H. E. KENDALL Plant Pat. 3,734
AVOCADO TREE
Filed Feb. 13, 1974
*Miguel*
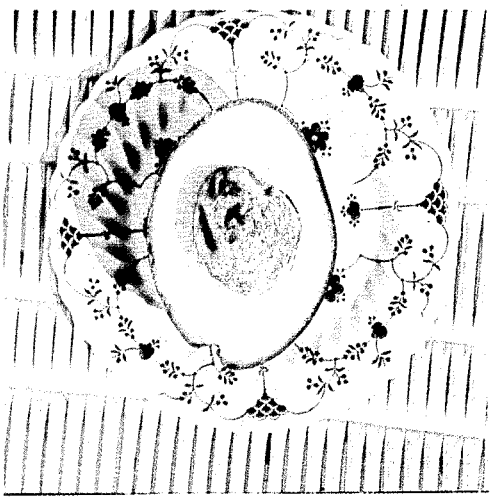
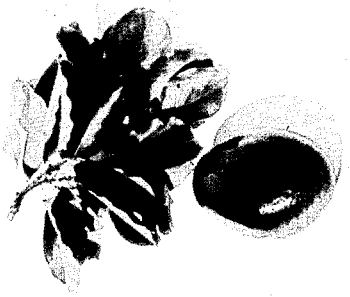
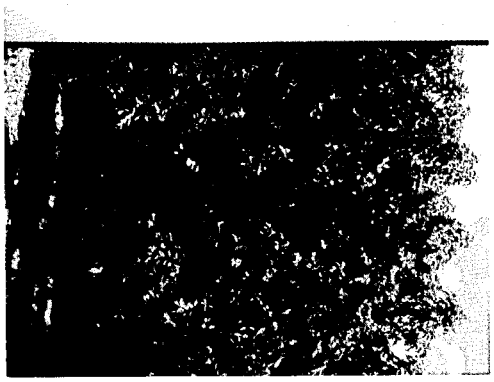

United States Patent

Plant Pat. 3,734
Patented June 24, 1975

3,734

AVOCADO TREE

Harold E. Kendall, P.O. Box 458, Goulds, Fla. 33170

Filed Feb. 13, 1974, Ser. No. 442,052
Int. Cl. A01h *5/03*
U.S. Cl. Plt—44 1 Claim This discovery pertains to a new and distinct variety of avocado tree which has many highly desirable characteristics. This new variety was discovered in a cultivated area in my Fort Drum Grove in South Dade County, Florida. While the original tree is a seedling of unknown parentage, it appears to be mostly of the West Indian race. The variety has been asexually reproduced at Coral Reef Nurseries, operated by me in Goulds, Dade County, Fla., where scions were budded to seedling trees. Other scions were grafted onto trees in groves operated by me in the Goulds-Princeton, Dade County, Fla., area.

This new variety is very desirable since it fills a demand for a large, good quality, yellow flesh avocado in certain markets during the late summer and early fall months. It matures at the time of year when there is presently a lack of a large, good quality, productive variety of avocado in Florida.

The accompanying illustrations show a specimen of the fruit cut in half, the individual fruit, the individual fruit and foliage and the orginal parent tree.

A description of the new variety follows:

SCIENTIFIC NAME

*Persea americana* (The Miguel).

RACE

West Indian parentage.

TREE

Trees are vigorous, branching freely and making a fairly spreading tree when mature. The leaves are large, mostly lanceolate, dark green and have a slight crinkle along the margins. Leaves are fairly close, averaging about one-half inch between nodes.

Trees bloom very early and profusely beginning about the end of January and usually continue to bloom through the month of March. The flowers are Type B.

Fruit is borne on single stems with an occasional cluster of two to a stem. Most fruits hang inside the tree so that there is very little chance of sunburn damage. Susceptibility to avocado scab (*Sphaceloma persea*) is low and the skin stays clean by applying two or three fungicidal sprays before harvesting.

FRUIT

*Oustide*: The fruit is large. The skin is dark green, smooth, shiny, slightly leathery, and is very easy to separate from the flesh. A few narrow streaks, which are slightly lighter in color than the surrounding skin and that run from the stem to the stylar end, are usually present. The skin is free of cork lenticels in almost all the fruits.

Fruit weight varies from 20 to 48 ounces. Size increases as the season progresses. The shape of this fruit is elliptical, having a cleft at the stylar end. The average dimensions for a 31 ounce fruit are 4.3″ wide and 5.9″ long, and 4.9″ by 5.7″ respectively for a 40 ounce fruit.

*Inside*: The flesh is yellow, smooth, buttery, and is free of brown fibers in most fruits. The width of the dark green interior ring around the skin varies from 0.1″ to 0.2″, and the flesh thickness for 0.8″ to 0.9″ for a 31 ounce fruit. Ring and flesh widths for a 40 ounce fruit are 0.1″ to 0.2″, and 0.9″ to 1.1″ respectively. Flesh thickness dimensions are ⅛″, 0.9″, and 1.5″ at the stem end, equator and stylar end areas respectively for a 31 ounce fruit, while the respective dimensions for a 40 ounce fruit are 1.7″, 1″, and 1.7″.

Seeds are of medium size and tight in the cavity. The seed of a 31 ounce fruit is 6.3″ wide and 6.7″ long, while that of a 40 ounce fruit is 7.5″ wide and 6.8″ long. The seed weight of a 31 ounce fruit is 4.2 ounces and that of a 40 ounce fruit is 6.4 ounces.

FRUIT QUALITY

Softening is regular with an absence of hard areas. The fruit retains its external dark green color at the soft stage; this is a desirable trait from the marketing viewpoint. Flavor is excellent to exquisite, having a nutty taste. The flesh is smooth. It takes 6 to 10 days at 70° Fahrenheit from picking to softening. The fruit seems to ship well and shows no damage from extended refrigeration at 45° Fahrenheit.

COMPARISON WITH OTHER VARIETIES

| Variety | Season | Size, ounces | Flower, type | Appearance |
|---|---|---|---|---|
| Subject variety (Miguel). | Late August thru September. | 20-48 | B | Large, shiny, dark, slightly leathery green, with cleft. |
| Lisa (unpatented). | -----do--------- | 19-14 | B | Small, smooth, thin skin, round to oval. |
| Meya (Plant Pat. No. 3116). | January thru March. | 10-14 | B | Oblongate, small, dark green pebbled with prominate lenticels. |
| Zio (Plant Pat. No. 3117). | December to February. | 9-13 | B | Small, rough, pebbled dark green oblong. |

Having thus described my discovery, I claim:

1. A new and distinct variety of avocado tree, substantially as shown and described.

No refernces cited.

ROBERT E. BAGWILL, Examiner